United States Patent [19]
Bär et al.

[11] 4,025,631
[45] May 24, 1977

[54] DIHYDROQUINOLINE DERIVATIVES OF ANTIOXIDANT ACTIVITY

[75] Inventors: Vilmos Bär; Jenō Mercz; János Szvoboda; Zsuszanna B. Pollák; Jakab Mátyás, all of Budapest, Hungary

[73] Assignee: Material Ksz., Budapest, Hungary

[22] Filed: Jan. 2, 1975

[21] Appl. No.: 538,294

Related U.S. Application Data

[62] Division of Ser. No. 285,168, Aug. 31, 1972, abandoned.

[30] Foreign Application Priority Data

Sept. 7, 1971 Hungary .................................. 2642

[52] U.S. Cl. .............................. 424/258; 252/401; 260/3; 426/545
[51] Int. Cl.$^2$ ......................................... A61K 31/47
[58] Field of Search .................................... 424/258

[56] References Cited

OTHER PUBLICATIONS

Bar et al., Chem. Abst., vol. 79 (1973), p. 92, 285d.
Anon, Chem. Abst., vol. 71 (1969), p. 20983s.
Hodge et al., Chem. Abst., vol. 66 (1967), p. 17621p.

*Primary Examiner*—Sam Rosen
*Attorney, Agent, or Firm*—Blum, Moscovitz, Friedman & Kaplan

[57] ABSTRACT

This invention relates to novel condensation products of aldehydes and tri- or tetramethyl-1,2-dihydroquinolines of antioxidant activity, as well as to a process for the preparation of such products. The novel compounds are nontoxic, exert their activity both in living organisms and in inanimate objects, and can be used in the chemical and food industry, as well as for therapeutic purposes.

6 Claims, No Drawings

DIHYDROQUINOLINE DERIVATIVES OF ANTIOXIDANT ACTIVITY

This is a division of application Ser. No. 285,168, filed Aug. 31, 1972, now abandoned.

BACKGROUND OF THE INVENTION

In the last few years the use of antioxidants has attained greater and greater importance, not only in industry, but also in agriculture, as well as in human and veterinary therapy. In the industrial field, and particularly in the rubber and plastic industry, there is an increasing demand for specific antioxidants compatible with different products and stabilizing to a high degree the advantageous physical properties of said products against oxidative damge. Antioxidants usable in the food industry and for medical purposes in human and veterinary therapy should satisfy several other requirements besides high activity, which, however, in some instances are in contravention with each other, or can only be combined with great difficulty. The most important special requirements which should be fulfilled by these antioxidants are the following: extremely low toxicity against living oganisms, wide spectrum of activity, and high compatibility with a wide range of substances. A particularly important field where such antioxidants are used is the stabilization of foodstuffs and mixtures of foodstuffs containing, besides the easily decomposing organic substances and fats and oils sensitive to oxidation, also metal salts and trace elements, etc. catalyzing the oxidation processes. Such antioxidants have also particular value in the stabilizing of meat- and fish-meal and of other products of the food industry, and in the stabilizing of medicines containing fats, oils and vitamins, which are extremely sensitive to oxidation processes. The antioxidants usable for the above purposes should exert their protective activity in a wide range of substances and they should maintain their effect also under conditions which normally lead to the decrease of activity.

In the last few years the demaand for antioxidants of special effects has also been increased due to the recognition of the important role of oxidation processes, and, respectively, the harmful effects of peroxides formed in such oxidation processes displayed in living organisms. Such peroxides play an important role in the etiology of several pathological conditions of animals; e.g., in the exudative diathesis of poultry, liver diseases, yellowing of the fatty tissues in pigs, inhibiting the development of certain nematode larvae, etc. On the basis of these findings certain antioxidants have already been used with great success in the treatment of such pathological conditions. There was also recognized a causative relationship between the activity of antioxidants and of certain vitamins, first of all of vitamin E, and antioxidants have already been used with good results in the treatment of encephalomalacia of poultry.

As a result of several extended investigations for preparing antioxidants usable in biological systems and also, for example, for the stabilizing of foodstuff mixtures, the use of N,N'-diphenyl-p-phenylenediamine (DPPD) was proposed in the fifties. This compound, however, has not proved to be useful for the above purposes due to its toxicity, cancer-inducing effect and relatively low activity. There have also been proposed other compounds, namely, 2,6-di-tert.butyl-4-hydroxytoluene (BHT), a mixture of isomeric 2-tert.butyl-4-hydroxy-anisol and 3-tert. butyl-4-hydroxy-anisol (BHA), mercapto-ethylamine, polyhydroxydiphenyl, gallic acid alkyl esters, and 6-ethoxy-2,2,4-trimethyl-1,2-dihydroquinoline (EMQ) for the above purposes. Among these compounds first of all BHT and EMQ have found an extended use in the practice for the stabilizing of foodstuff mixtures and meat- and fish-meal, as well as for medical purposes in human and veterinary therapy. These compounds, however, do not meet the severe requirements with respect to toxicity. According to the proposals of WHO/FAO Nutrition Meetings Report Series No. 40 A, B, C, WHO/FAQ-DAU 67.29, only compounds having an $LD_{50}$ value higher than 5 g./kg. body weight can be used in the food industry and for therapeutical purposes. The $LD_{50}$ values of BHT and EMQ are, on the other hand, the following — measured according to the Korber method, modified by Cornfield:

BHT 0.892 ± 0.12 g./kg.
EMQ 2.23 ± 0.30 g./kg.

Besides the fact that the acute toxicity of these compounds exceeds the acceptable value, the investigations carried out on chronic toxicity closed also with unfavorable results. According to the results of investigations carried out in the Hungarian National Pharmaceutical Institute, EMQ, when administered for a longer period in a dose of 0.56 g./kg. may cause appetite lowering, and lowers the gain in weight. Similar unfavorable results have been observed when administering EMQ into rats for 14 days in a dose of 0.50 g./kg.: the appetite of the animals was lowered; moreover an increase in size of the liver was observed. (See I. F. Gaunt et al.; Food and Cosmetic Tox., 3, 445–446; 1965.) It was also observed that when administering BHT, the cholesterol-synthesis in the liver as well as the endogenous epoxidation increases; moreover, this compound stimulates the endogenous production of fatty acids and $\beta$-oxidation, and increases the gestation period. As an aftereffect, the appearance of anophthalmia was observed, indicating that the compound exerts a teratogeneous effect. (See G. Pascal et al.; Ann. Nutr. Alim., 23, 15–62; 1969.)

A further disadvantage of EMQ is that this compound is a liquid, which makes its use in heterogeneous phase more difficult and expensive. On the other hand, BHT has the disadvantage that in certain fields of application, e.g., in the prophylaxis and treatment of encephalomalacia of poultries, it has far lower activity than EMQ.

The above facts show unambiguously that even the best of the known antioxidants having an extended practical use, i.e., BHT and EMQ, cannot meet the severe requirements of nutrition, catering and therapy. Consequently, there still exists a great demand for active antioxidants usable for the above purposes.

SUMMARY OF THE INVENTION

The novel compounds of the invention are characterized by the general formula (I)

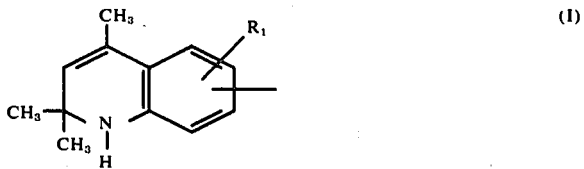

-continued

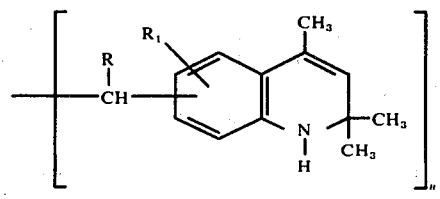

wherein
R represents hydrogen or a lower alkyl group of 1 to 4 carbon atoms,
$R_1$ represents hydrogen or a methyl group which may be attached in any of the free positions to the ring system with the exception of position 6, and
n is 1, 2 or 3.

According to the process of the invention the compounds of the general formula (I) are prepared by reacting 2,2,4-trimethyl-1,2-dihydroquinoline or a derivative thereof containing a further methyl group with an aldehyde of the general formula

R—CHO wherein R has the same meaning as defined above. The reaction is carried out at temperatures between room temperature and the boiling point of the mixture, in the presence of a catalyst, preferably of an acid or of a metal oxide or halide deposited on a support of high specific surface area. The molar ratios of the starting substances, as well as the reaction conditions, are adjusted in accordance with the desired degree of polymerization.

As it turns out from general formula (I), the condensation products of the invention contain 2 to 4 dihydroquionoline units connected to each other through methylene bridges. These methylene bridges are attached in the majority of cases to position 6 of the ring system; in some instances, however, they may be attached to other positions, particularly to position 8 of the ring system.

An object of the invention is to provide a class of compounds suitable for use as an antioxidant in foodstuffs and in the treatment of disease in humans and in animals.

Another object of the invention is to provide a method of manufacture of said class of compounds.

A further object of the invention is a pharmaceutical product of antioxidant activity suitable for use in combination with radiation in the treatment of malignant process.

The invention accordingly comprises the several steps and the relation of one or more of such steps with respect to each of the others, and the composition possessing the features, properties, and the relation of constituents which are exemplified in the following detailed disclosure, and the scope of the invention will be indicated in the claims.

DESCRIPTION OF THE PREFERRED EMBODIMENTS

We have found, unexpectedly, that the compounds of the general formula (I) are nontoxic and exert their activity both in living organisms and in inanimate objects; consequently they can be utilized in the chemical and food industry, as well as for therapeutic purposes, with good results and with greater advantages than the hitherto-known substances.

The compounds of the general formula (I) can be prepared by condensing 2,2,4-trimethyl-1,2-dihydroquinoline or a derivative of this compound containing a further methyl group but being unsubstituted in the 6-position, e.g., 2,2,4,7-tetramethyl-1,2-dihydroquinoline, or a salt of such compounds with an appropriate aliphatic aldehyde. The condensation reaction is carried out preferably in a solvent medium in the presence of an acid catalyst, at temperatures between room temperature and the boiling point of the reaction mixture. The aldehyde is used generally in an amount of 0.5 to 1.0 moles, preferably in an amount of 0.5 to 0.6 moles per mole of dihydroquinoline compound. In this reaction there are formed condensation products consisting of 2 to 4 dihydroquinoline units connected to each other through methylene bridges, where the methylene bridges may be attached to any position of the aromatic ring, but mainly to position 6. In contradistinction to the monomeric compounds, i.e., 2,2,4-trimethyl-1,2-dihydroquinoline and its 6-ethoxy-derivative (EMQ), the above condensation products show no detectable toxicity either acute or chronic; moreover the condensation products retain the good antioxidant effect of the monomeric dihydroquinoline of analogous structure, e.g., that of EMQ, or they are even more effective than the corresponding monomers.

A further advantage of the condensation products is that they possess also chelate-forming ability; accordingly, they can bind the heavy metal ions and particularly copper ions which would otherwise promote oxidation in the systems to be protected. Moreover, the condensation products — similarly to the amine-type monomeric antioxidants — are able to decompose the hydroperoxides generated in oxidation processes and to bind the thus-formed free radicals. The degree of condensation of the dihydroquinoline — aldehyde condensation products characterized essentially by the general formula (I) — i.e., the number of dihydroquinoline units present in the product, depends first of all on the reaction conditions utilized in the condensation, as well as on the molar ratio of the starting substances. Conducting the condensation reaction under the conditions described above, a mixture consisting mainly of molecules containing 2 to 4 dihydroquinoline units is obtained.

Such antioxidants containing condensation products of the general formula (I) were not known up to now. Monomeric 2,2,4-trimethyl-1,2-dihydroquinoline, used as starting compound for the condensation products of the invention, is a known substance. The preparation and properties of this starting substance were described, for example, by Bayer (J. prakt. Chem., 2, 33, 401; 1886) and by Combes (Bull. Soc. Chim. France, 49, 89; 1888). W. H. Cliffe (J. Chem. Soc. London, 1933, 1329) describes a condensation reaction of the above compound with formaldehyde and with some aromatic amines, respectively; the condensation with formaldehyde was carried out, however, at a temperature of 20° C for at least 2 hours, using 4 moles of formaldehyde per mole of dihydroquinoline derivative. Under such conditions, however, compounds analogous to the general formula (I) of secondary amine structure do not form, but in the formed product the dihydroquinoline units are connected with each other through methylene bridges attached to the heterocyclic nitrogen atom. These compounds of tertiary amine type have quite different chemical behavior than those of the general formula (I), e.g., they cannot be dissolved in hydrochloric acid, have a basicity lower by one order of magnitude than the secondary amine type compounds, and show quite different chromatographical characteristics. The tertiary amine type compounds have no antioxidant effect at all. The same product of tertiary amine type was also described by D. Craig (J. Am. Chem. Soc. 60, 1458–1465, 1938).

Consequently, the condensation products of 2,2,4-trimethyl-1,2-dihydroquinoline and its substituted derivatives formed with formaldehyde or with other aliphatic aldehydes, having essentially a structure analogous to that described in general formula (I) and showing secondary amine character, are also new substances.

The invention relates further to the preparation of condensation products of aldehydes and 2,2,4-trimethyl-1,2-dihydroquinoline or its derivatives containing a further methyl group but being unsubstituted in the 6 position, having antioxidant effect and corresponding essentially to the general formula (I), wherein R, $R_1$ and n have the same meanings as defined above, characterized in that 2,2,4-trimethyl-1,2-dihydroquinoline or a derivative thereof containing a further methyl group but being unsubstituted in the 6 position, or an acid addition salt of these compounds, is condensed with an aldehyde of the general formula

wherein R has the same meaning as defined above, in the presence of a solvent and preferably of an acidic catalyst, at temperatures between room temperature and the boiling point of the reaction mixture, and the aldehyde compound is used preferably in an amount of 0.5 to 1.0 moles per mole of the dihydroquinoline compound. Paraformaldehyde can be used in place of formaldehyde.

Since under the conditions of the process according to the invention the 2,2,4-trimethyl-1,2-dihydroquinoline molecules are connected to the methylene bridge formed from the aldehyde mainly on the carbon atom at position 6, when starting from a compound wherein $R_1$ and R each represent hydrogen, bis-(2,2,4-trimethyl-1,2-dihydroquinoline-6)-methane — hereinafter referred to as XAX — the corresponding derivatives of higher condensation grade, containing 3 or 4 dihydroquinoline units, or, respectively, a mixture of these products is obtained. According to our observation, in the derivatives of higher condensation grade the further methylene bridges are attached mainly to the 8 position of the dihydroquinoline ring.

When the condensation reaction terminates, the non-reacted monomeric dihydroquinoline starting substance is removed from the reaction mixture. The unreacted substance can be removed, e.g., by steam distillation, preferably with superheated steam, by azeotropic distillation, e.g., in the presence of toluene or of an acetone-ethanol mixture, or by extraction with an aqueous medium of pH 3 to 4.5; at these pH values only the unreacted starting substance enters into solution.

The product obtained after this purification step necessary for the removal of the unreacted starting substances can generally be used as antioxidant for the majority of technical purposes without any further treatment. Should the product, however, be used in a field where a high purity grade is required, e.g., in the food or pharmaceutical industry, the free bases or their addition salts with pharmaceutically acceptable acids can be purified by recrystallization from aqueous or nonaqueous solvents, or by precipitation of the salt from the solution of the free base in an organic solvent, e.g., with concentrated hydrochloric acid. The precipitated acid addition salt of the antioxidant can be washed with an aqueous acid; thereafter the base can be liberated using an alkali.

The new antioxidants of the invention are crystalline solids, the physical properties of which are very advantageous from practical points of view. These compounds are well soluble in the majority of the usual organic solvents; e.g., in benzene and other hydrocarbons, in carbon tetrachloride, chloroform, acetone, glacial acetic acid, dioxane, etc. Depending on the degree of polymerization, some of the compounds can even be dissolved in methanol or ethanol. The new antioxidants are insoluble in water and in dilute aqueous alkaline solutions, while in dilute acids they form acid addition salts. The products are tasteless and odorless, noncorrosive, inert to organic substances and have no discolorizing effect. Moreover they can easily be dispersed in rubber and in related substances, are not liable to migration and blooming, and are completely harmless to living organisms. Due to these advantageous properties, the products of the invention can favorably be used for stabilizing plastics and rubbers, for the protection of foodstuffs and nutriments against oxidative damage, as well as for therapeutic purposes.

Accordingly, bis-(2,2,4-trimethyl-1,2-dihydroquinolyl-6)-methane (XAX) and its derivatives containing a further methyl group, as well as the acid addition salts of these compounds, can be used as antioxidants with great advantages both in industry and for catering and for therapeutic purposes.

Due to their advantageous properties, these compounds can be used as antioxidants in many fields of industry, especially in the rubber industry. The above compounds exert a favorable protection, for example, on vulcanized rubber products against oxidative attack and aging, as well as against damage caused by the action of heat and light. They do not show any blooming in the finished rubber products even when added in amounts of 5% by weight, while on the other hand, they grant a complete protection against oxidative damages in concentrations as low as 0.5 to 1% by weight. Due to the fact that the substances cause no toxic symptoms at all, they can also be incorporated into rubber products being in a direct contact with living organisms. The novel antioxidants can also be used with good results for protection against oxidative damages and aging in pneumatic tires of vehicles, rubber carpets, conveyor bands, rubber pipes, shoe soles and other technical products made of rubber, as well as in toys, sanitary products, etc. made of plastics.

Since the novel compounds are completely nontoxic, they can be used with great advantage in animal husbandry and in the food industry, as well as in therapy. On the basis of the investigations carried out on the acute and chronic toxicity of these new active agents, it can be stated that they are completely free of the disadvantages of the hitherto-known antioxidants mentioned above, first of all as regards their use in therapy. Thus, for example, XAX shows no toxic symptoms on rats even in a dose of 5 g./kg. body weight, and after a continuous administration of daily doses of 0.25 mg./kg. of XAX for three weeks, no damaging of tissues or cells could be observed. No harmful effects could be observed after the continuous administration of the same dose of XAX to rats for 90 days. Neither the weight gain nor the blood picture of the animals was harmfully affected, and no excessive weight gain of some organs of the animals could be observed, in comparison with the animals kept under identical conditions but not treated with XAX.

The antioxidant effect of the new substances shown in foodstuffs and nutriments was investigated on fishmeal samples. Comparative experiments were carried out with known compounds having high antioxidant effect but unsuitable for this purpose due to their toxicty (6-ethoxy-2,2,4-trimethyl-1,2-dihydroquinoline (EMQ) and 2,6-di-tert.butyl-4-hydroxy-toluene (BHT)). In these experiments the oxygen uptake of fish-meal samples containing the various antioxidants was determined in a Warburg apparatus at 29° C, and the results were compared with those measured on samples containing no antioxidant. The peroxide number of samples treated with oxygen was also determined. The data obtained are listed in Table I.

TABLE I

| Sample | Oxygen Uptake (decrease of $O_2$ pressure, mmHg) | Peroxide Number (calculated for 1 g. of fish meal) |
| --- | --- | --- |
| 10 g. of fish meal (control) | 19.5 | 7.83 |
| 10 g. of fish meal + 0.04 g. of EMQ | 23.5 | 2.87 |
| 10 g. of fish meal + 0.04 g. of BHT | 16.5 | 3.42 |
| 10 g. of fish meal + 0.04 g. of XAX | 11.5 | 1.54 |

From the results listed in Table I it is evident that the fish-meal samples stabilized with XAX, a product of the invention, absorb far lower amounts of oxygen than those containing known antioxidants or containing no antioxidant at all. A very important fact is that the samples stabilized with the product of the invention show a far lower peroxide number after being treated with oxygen than the others. These results prove that the antioxidant of the invention exerts a far higher protection action on fish meal, a substance containing 30% unsaturated oils and highly sensitive to oxidation, than the hitherto-known antioxidants.

The new antioxidants of the invention show particularly important advantages in their therapeutic use. These advantages are only partly due to the fact that the compounds are completely nontoxic; consequently they can be used in therapy without any risk. It is even more important that the new compounds are far superior to the antioxidants hitherto used in therapy with respect both to their activity and to their therapeutic spectrum.

From a therapeutic point of view it is extremely important that the novel antioxidants possess also a serum cholesterol-lowering effect. Due to this fact they can also be used for the prophylaxis and treatment of arteriosclerois. This effect of the new substances was investigated on rabbits treated with 1 g. of cholesterol per day. The animals were treated for 70 or 105 days with daily doses of 0.06 g./kg. of XAX. In the control animals, which did not receive XAX, a considerable increase of the serum cholesterol level could be observed due to the continuous administration of cholesterol, while in the case of animals treated with the active agent, the cholesterol level of the blood decreased to a great extent. Using the hitherto-known antioxidants, this very favorable and important effect could not be reached at all.

Another important and unexpected property of the new substances is that they exert radiosensibilizing effect. Mice fed with a foodstuff containing 0.03 to 0.1 g./kg. of the antioxidant of the invention showed a far greater sensitivity over an irradiation with a dose of 700 r than the control animals fed with a foodstuff of the same composition but containing no active agent. On the basis of this property, the new compounds can also be used for the potentiating of the effect of irradiation therapy. Obviously this effect of the novel compounds can explain the fact that the appearance of malignant tumors in animals treated with minimum irradiation doses for a long period could be suppressed by adding XAX to the animals, in comparison with the control animals irradiated in the same way but not treated with XAX.

All the above results show that the new compounds of the invention, first of all bis-(2,2,4-trimethyl-1,2-dihydroquinolyl-6)-methane (XAX) and its therapeutically acceptable acid addition salts, besides their industrial use, can also be used in therapy with good results.

In their therapeutic use, the nontoxic character of the compounds makes it possible to administer them in relatively high doses.

The physicochemical properties, e.g., the molecular weight and the melting point of the tri- and tetramethyl-1,2-dihydroquinoline-aldehyde condensation products, of the invention depend first of all on the degree of polymerization, i.e., on the value of n in the general formula (I). The antioxidant activity of the compounds is, however, not affected by their degree of polymerization. Due to the above fact it is of no importance from practical points of view to separate the compounds containing two dihydroquinoline units from those having a higher degree of polymerization. For analytical purposes, the separation of condensation products can be carried out by several recrystallization steps or by chromatography.

The invention is further elucidated by the aid of the following nonlimiting examples.

EXAMPLE 1

346 parts by weight of 2,2,4-trimethyl-1,2-dihydroquinoline, 500 parts by weight of methanol and 95 parts by weight of 35% formaldehyde solution are introduced into a jacketed reactor; thereafter 250 parts by weight of concentrated hydrochloric acid are added slowly into the stirred reaction mixture. During the addition care must be taken that the temperature of the mixture should not exceed 40° C. After the addition the mixture is stirred for 4 hours, holding the temperature between 30° and 40° C. The obtained crude mixture, containing about 8 to 15% unreacted 2,2,4-trimethyl-1,2-dihydroquinoline, is diluted with a two fold amount of water, filtered, and the product is precipitated by adding sodium hydroxide to the mixture. The obtained solid product is separated, dissolved in toluene, and the solvent and such unreacted starting substance as may be present are removed by steam distillation carried out with superheated steam. The residue is recrystallized from hexane. 290 parts by weight of a product are obtained, consisting mainly of bis-(2,2,4-trimethyl-1,2-dihydroquinolyl-6)-methane and containing also minor amounts of products of higher degree of polymerization. The product melts at 83° to 86° C.

Analysis: Calculated for $C_{25}H_{30}N_2$: C = 83.80%; H = 9.38%; N = 7.82%; Found: C = 81.65%; H = 8.34%; N = 10.27%

The molecular weight of the product calculated on the basis of the boiling point increase is 385, while the molecular weight corresponding to the above formula is 358. The difference is due to the presence of substances of higher degree of polymerization.

EXAMPLE 2

One proceeds essentially as described in Example 1, with the difference that the crude product precipitated with sodium hydroxide is dissolved in benzene, and the benzene solution is washed several times with an aqueous hydrochloric acid solution of pH = 4 in order to remove such unreacted starting substances as may be present. Benzene is removed by distillation and the residue is recrystallized from a mixture of acetone and water. The amount and the quality of the obtained product correspond to that obtained in Example 1.

EXAMPLE 3

One proceeds essentially as described in Example 1, with the difference that the pH of the mixture diluted with twofold amount of water is adjusted with sodium hydroxide solution to 3 to 5. Under such conditions the product precipitates, while the unreacted starting compound remains in solution. The precipitated product is washed with water and dried. The obtained crude bis-(2,2,4-trimethyl-1,2-dihydroquinolyl-6)-methane is sufficiently pure for technical purposes. For analytical purposes, or when the product is intended for use in the food industry or in therapy, it can be recrystallized as described above.

EXAMPLE 4

346 parts by weight of 2,2,4-trimethyl-1,2-dihydroquinoline, 346 parts by weight of methanol, 346 parts by weight of water and 95 parts by weight of 35% formaldehyde solution are introduced into the reactor used in Example 1, and 180 parts by weight of concentrated hydrochloric acid are added slowly to the mixture under vigorous cooling. During the addition the temperature of the mixture should be kept below 50° C by external cooling. After 16 hours of reaction the mixture is diluted with 1000 parts by weight of acetone, and the pH of the obtained mixture is adjusted to about 10 by adding 50% aqueous sodium hydroxide solution. The aqueous-alkaline phase and the nondissolved sodium chloride are separated, and the solvent is evaporated from the organic phase. The antioxidant obtained as a residue is mixed with water, heated to 150° C in a closed vessel under pressure; thereafter it is cooled, and the solidified product is pulverized. 340 parts by weight of a product are obtained, having a quality identical to that obtained in Example 1.

EXAMPLE 5

An emulsion made of 346 parts by weight of 2,2,4-trimethyl-1,2-dihydroquinoline, 115 parts by weight of white spirit and 95 parts by weight of a 35% formaldehyde solution is introduced into the reactor used in Example 1, and 25 parts by weight of a 50% sulfuric acid solution are added slowly to the emulsion under vigorous stirring. The exothermic reaction subsides after about 1 to 2 hours. Then the mixture is stirred for further 8 hours at 85° to 95° C; thereafter it is alkalinized to a pH of 9 to 10 with sodium hydroxide. The condensation product, which separates in the form of the free base, as well as the sodium chloride formed are collected by filtration or centrifugation, sodium chloride is removed from the solids by washing with water, and the obtained base is dissolved in hot water and allowed to cool. 341 parts by weight of an antioxidant are obtained. The product has a molecular weight of 358 after recrystallization from white spirit.

EXAMPLE 6

One proceeds essentially as described in the above examples, with the difference that the unreacted starting substance is not removed from the residue by steam distillation or by extraction, but a sample of the obtained crude mixture is subjected to thin layer chromatography in 5% benzene solution in order to determine the amount of unreacted 2,2,4-trimethyl-1,2-dihydroquinoline present. The chromatography is carried out on activated silica gel layer, using a mixture of 95% benzene, 4.97% of butanol and 0.03% of water as eluting agent. The spots are developed with dilute potassium permanganate solution. In the comparative tests, samples of 2,2,4-trimethyl-1,2-dihydroquinoline solutions of known concentration are used. Thereafter the crude reaction mixture, obtained as described above, is mixed with 0.5 moles of formaldehyde per mole of 2,2,4-trimethyl-1,2-dihydroquinoline present, and the mixture is refluxed for 1 to 2 hours. The mixture is worked up as described in the above examples.

EXAMPLE 7

354 parts by weight of 2,2,4,7-tetramethyl-1,2-dihydroquinoline, 600 parts by weight of methanol and 48 parts by weight of acetaldehyde are introduced into the reactor used in Example 1, and a reflux condenser is attached to the reactor. Thereafter 210 parts by weight of a 33–34% hydrochloric acid solution are added slowly over the course of 2 hours to the stirred and cooled mixture. During the addition care must be taken that the temperature of the mixture should not exceed 50° C. When the addition is complete, the mixture is refluxed for 5 hours.

The pH of the obtained mixture is adjusted to 9 to 10 with 50% sodium hydroxide solution; thereafter the solvent is distilled off. The residual product is dissolved in water at 120° to 140° C under superatmospheric pressure; thereafter the vessel is vented, whereupon the unreacted starting substance leaves the system together with the water vapors. 320 parts by weight of a yellowish-brown product are obtained, having a molecular weight about 450. When heating, the product begins to soften at 82° to 84° C, but it has no sharp melting point. The product is well soluble in warm vegetable oils and fats, and its oxidation-inhibiting activity, measured in Warburg apparatus, is about 80% of the activity of XAX.

In the above process one may also use 900 parts by weight of 80% acetic acid in place of methanol, whereupon similar results are obtained.

EXAMPLE 8

358 parts by weight of bis-(2,2,4-trimethyl-1,2,-dihydroquinolyl-6)-methane are dissolved in 700 parts by weight of benzene, and 36.5 parts by weight of dry gaseous hydrogen chloride are introduced into the solution. The monohydrochloride, separating with a quantitative yield, is filtered off and dried. The obtained monohydrochloride is well soluble in water and alcohol, and melts at 219° C after recrystallization from ethanol.

EXAMPLE 9

358 parts by weight of bis-(2,2,4-trimethyl-1,2-dihydroquinolyl-6)-methane are dissolved in 1000 parts of acetone, and 73 parts by weight of dry gaseous hydrogen chloride are introduced into the solution. The dihydrochloride separating in crystalline form is filtered off and recrystallized from water or ethanol. The thus-obtained dihydrochloride, a substance soluble in water and alcohol, melts at 235° C.

In the above experiment one can also use an equivalent amount of at least 30% hydrochloric acid in place of dry hydrogen chloride, whereupon similar results are obtained.

One proceeds as described above, with the difference that in place of hydrochloric acid, 98 parts by weight of concentrated sulfuric acid are added to the solution of the base. The obtained sulfuric acid salt of XAX is soluble in water and alcohol.

EXAMPLE 10

Preparation of tablets:

500 g. of bis-(2,2,4-trimethyl-1,2-dihydroquinolyl-6)-methane, purified by several recrystallization steps, are mixed with 472 g. of potato starch, the mixture is wetted with an aqueous solution of 9 g. of gelatine, and the wet mixture is passed through a sieve. The granules are dried, mixed with 30g. of talc, and pressed into 1000 tablets each weighing 1 g. and containing 0.5 g. of the active agent. In order to facilitate halving, the tablets are provided with a dividing line.

EXAMPLE 11

Preparating of injectable solution for intravenous use:

50 g. of bis-(2,2,4-trimethyl-1,2-dihydroquinolyl-6)-methane-dihydrochloride, a product purified by several recrystallization steps, are dissolved in 450 ml. of isotonic salt solution; the solution is filtered, filled into vials, and the filled vials are sterilized in an autoclave at 120° C.

EXAMPLE 12

Preparation of an oily solution for oral administration:

20 g. of bis-(2,2,4-trimethyl-1,2-dihydroquinolyl-6)-methane are dissolved in 480 g. of sunflower oil; the solution is filtered and sterilized.

EXAMPLE 13

Preparation of a medicated hard candy.

20 grams of bis-(2,2,4-trimethyl-1,2-dihydroquinolyl-6)-methane are dissolved in 480 grams of conventional hard candy composition while hot and liquid. The liquid is formed into lozenges and cooled.

It will thus be seen that the objects set forth above, among those made apparent from the preceding description, are efficiently attained and, since certain changes may be made in carrying out the above process and in the compounds set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A pharmaceutical product of antioxidant activity, usable in combination with radiation for the treatment of malignant processes, characterized by containing an effective amount of at least one compound of the formula (I)

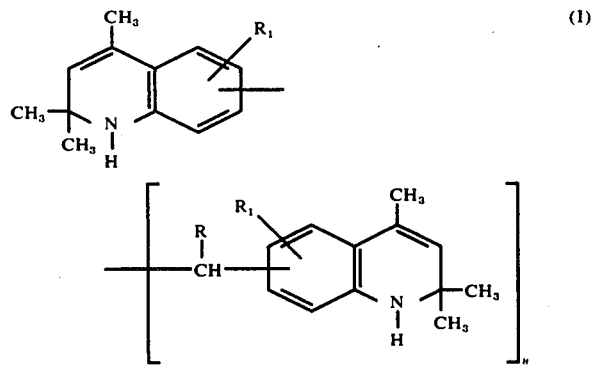

wherein
R represents hydrogen or a lower alkyl group of 1 to 4 carbon atoms,
$R_1$ represents hydrogen or a methyl group which may be attached to a carbon atom in any of the free positions to the ring system, with the exception of position 6, and
n is 1, 2 or 3 or a pharmaceutically acceptable acid addition salt thereof in combination with a pharmaceutically acceptable carrier.

2. A pharmaceutical product comprising at least one compound of the formula (I) as defined in claim 1, in tablet form.

3. A pharmaceutical product comprising at least one compound of the formula (I) as defined in claim 1, in a sterile isotonic salt solution suitable for intravenous injection.

4. A pharmaceutical product comprising at least one compound of the formula (I) as defined in claim 1, dissolved in an edible oil and suitable for oral administration.

5. A pharmaceutical product comprising at least one compound of the formula (I) as defined in claim 1, incorporated in a lozenge for oral use.

6. A pharmaceutical product as defined in claim 1, where R and $R_1$ are H and n is 1.

* * * * *